United States Patent
Boling et al.

(10) Patent No.: US 7,844,345 B2
(45) Date of Patent: Nov. 30, 2010

(54) DRUG ELUTING LEAD SYSTEMS

(75) Inventors: C. Lance Boling, San Jose, CA (US); Daniel Chao, San Francisco, CA (US); Martha J. Morrell, Atherton, CA (US); Benjamin D. Pless, Mountain View, CA (US); Thomas K. Tcheng, Pleasant Hill, CA (US); Brett M. Wingeier, San Francisco, CA (US)

(73) Assignee: NeuroPace, Inc., Mountain View, CA (US)

(*) Notice: Subject to any disclaimer, the term of this patent is extended or adjusted under 35 U.S.C. 154(b) by 854 days.

(21) Appl. No.: 11/704,549

(22) Filed: Feb. 8, 2007

(65) Prior Publication Data

US 2008/0195227 A1    Aug. 14, 2008

(51) Int. Cl.
  *A61N 1/00* (2006.01)
(52) U.S. Cl. ...................................... 607/116
(58) Field of Classification Search ............... 600/37, 600/372; 604/21; 607/3, 116, 119, 129
  See application file for complete search history.

(56) References Cited

U.S. PATENT DOCUMENTS

| | | | |
|---|---|---|---|
| 3,310,051 A | 3/1967 | Schulte | |
| 3,640,269 A | 2/1972 | Delgado | |
| 4,506,680 A | 3/1985 | Stokes | |
| 5,092,332 A | 3/1992 | Lee et al. | |
| 5,217,028 A | 6/1993 | Dutcher et al. | |
| 5,255,693 A | 10/1993 | Dutcher et al. | |
| 5,265,608 A | 11/1993 | Lee et al. | |
| 5,496,360 A | 3/1996 | Hoffmann et al. | |
| 5,713,847 A | 2/1998 | Howard, III et al. | |
| 5,755,758 A | 5/1998 | Woloszko et al. | |
| 5,834,051 A | 11/1998 | Woloszko et al. | |
| 5,836,935 A | 11/1998 | Ashton et al. | |
| 5,865,842 A | 2/1999 | Knuth et al. | |
| 6,006,124 A | 12/1999 | Fischell et al. | |
| 6,032,482 A | 3/2000 | Krauss | |
| 6,038,482 A | 3/2000 | Vachon | |
| 6,068,853 A | 5/2000 | Giannos et al. | |
| 6,073,048 A | 6/2000 | Kieval et al. | |

(Continued)

OTHER PUBLICATIONS

Anonymous. (2006). "Ommaya Reservoir," located at <http://health.enotes.com/cancer-encyclepedia/ommaya-reservoir>, last visited on Sep. 18, 2006, six pages.

(Continued)

*Primary Examiner*—George Manuel
*Assistant Examiner*—Robert N Wieland

(57) ABSTRACT

Medical electrical lead systems and related methods are described. The lead systems may be configured to be at least partially implanted in neural tissue of a subject, such as a brain of a subject. Some variations of the lead systems may comprise a lead body, an electrode connected to the lead body, and a bioactive agent. The electrode and/or lead body may comprise a substrate, and the bioactive agent may be supported by the substrate (e.g., by a substantial portion of the area of the substrate). Examples of bioactive agents that may be used in the lead system include antiproliferative agents, bactericidal agents, bacteriostatic agents, antiepileptic agents, and/or antifungal agents. Methods described herein may comprise coating a lead body and/or an electrode of a medical electrical lead system with at least one bioactive agent, where the lead body and the electrode are connected to each other.

40 Claims, 5 Drawing Sheets

U.S. PATENT DOCUMENTS

| | | | |
|---|---|---|---|
| 6,148,231 | A | 11/2000 | Henley |
| 6,168,801 | B1 | 1/2001 | Heil, Jr. et al. |
| 6,219,577 | B1 | 4/2001 | Brown, III et al. |
| 6,227,203 | B1 | 5/2001 | Rise et al. |
| 6,304,787 | B1 | 10/2001 | Kuzma et al. |
| 6,330,471 | B1 | 12/2001 | Higo et al. |
| 6,385,491 | B1 | 5/2002 | Lindemans et al. |
| 6,497,699 | B1 | 12/2002 | Ludvig et al. |
| 6,567,705 | B1 | 5/2003 | Stokes et al. |
| 6,571,125 | B2 | 5/2003 | Thompson |
| 6,635,045 | B2 | 10/2003 | Keusch et al. |
| 6,678,553 | B2 | 1/2004 | Lerner et al. |
| 6,685,648 | B2 | 2/2004 | Flaherty et al. |
| 6,726,678 | B1 | 4/2004 | Nelson et al. |
| 6,748,653 | B2 | 6/2004 | Lindemans et al. |
| 6,931,286 | B2 | 8/2005 | Sigg et al. |
| 6,944,497 | B2 | 9/2005 | Stypulkowski |
| 7,010,356 | B2 | 3/2006 | Jog et al. |
| 7,044,942 | B2 | 5/2006 | Jolly et al. |
| 7,066,904 | B2 | 6/2006 | Rosenthal et al. |
| 7,200,432 | B2 | 4/2007 | Lerner et al. |
| 7,241,283 | B2 | 7/2007 | Putz |
| 7,337,011 | B2 | 2/2008 | Stokes et al. |
| 2003/0236496 | A1 | 12/2003 | Samson et al. |
| 2004/0127942 | A1 | 7/2004 | Yomtov et al. |
| 2004/0248326 | A1 | 12/2004 | Ziaie et al. |
| 2005/0070985 | A1 | 3/2005 | Knapp et al. |
| 2005/0149157 | A1* | 7/2005 | Hunter et al. ............... 607/119 |
| 2005/0246003 | A1 | 11/2005 | Black et al. |
| 2005/0246004 | A1 | 11/2005 | Cameron et al. |
| 2005/0277912 | A1 | 12/2005 | John |
| 2006/0058856 | A1 | 3/2006 | Morrell |
| 2006/0095105 | A1 | 5/2006 | Jog et al. |
| 2006/0129204 | A1 | 6/2006 | Pless et al. |
| 2006/0155343 | A1 | 7/2006 | Vilims |
| 2006/0184143 | A1 | 8/2006 | Jolly et al. |
| 2007/0060815 | A1* | 3/2007 | Martin et al. ............... 600/372 |
| 2007/0088335 | A1 | 4/2007 | Jolly |
| 2007/0250136 | A1 | 10/2007 | Karunasiri et al. |
| 2008/0015540 | A1 | 1/2008 | Muni et al. |
| 2008/0033520 | A1 | 2/2008 | Jolly |
| 2008/0097280 | A1* | 4/2008 | Martin et al. ............... 604/21 |

OTHER PUBLICATIONS

Cavuoto, J. (Jan. 2002). "Biomaterials Key Factor in Next-Generation Electrodes," *Neurotech Business Report* 2(1):3-5.

Christensen, J. et al. (Oct. 2001). "Plasma Concentration of Topiramate Correlates with Cerebrospinal Fluid Concentration," *Therapeutic Drug Monitoring* 23(5):529-535.

Craighead, H.G. (Nov. 24, 2000). "Nanoelectromechanical Systems," *Science* 290:1532-1535.

Doose, D.R. et al. (2002). "Topiramate: Chemistry, Biotransformation, and Pharmacokinetics," Chapter 78, in *Antiepileptic Drugs*, $5^{th}$ Edition, Levy, R.H. et al. eds., Lippincott Williams & Wilkins: Philadelphia, PA, pp. 727-734.

Ghosh, S. et al. (May 2000). "Electrochemical Characterization of Poly(3,4-ethylene dioxythiophene) Based Conducting Hydrogel Networks," *J. of the Electrochem. Soc.* 147(5):1872-1877.

Gilmore, K. et al. (1994). "Preparation of Hydrogel/Conducting Polymer Composites," *Polymer Gels and Networks* 2(2):135-143.

Martin, D.C. et al. "Bio-Electronic Implantable Device Coating Applications," in White Paper: Bioactive Conducting Polymer Coatings for Biomedical Devices, University of Michigan, four pages. (in internal database as of Aug. 30, 2006).

Olsen, R.W. (2002). "Phenobarbital and Other Barbiturates: Mechanisms of Action," Chapter 50, in *Antiepileptic Drugs*, $5^{th}$ Edition, Levy, R.H. et al. eds., Lippincott Williams & Wilkins: Philadelphia, PA, pp. 489-495.

Pitt, W.G. et al. (Nov. 2004). "Ultrasonic Drug Delivery—A General Review," *Expert Opinion on Drug Delivery* 1(1):37-56.

Rusakov, D.A. et al. (May 1, 1998). "Extrasynaptic Glutamate Diffusion in the Hippocampus:Ultrastructural Constraints, Uptake, and Receptor Activation," *The J. of Neurosci.* 18(9):3158-3170.

Non-Final Office Action mailed on Sep. 8, 2009, for U.S. Appl. No. 11/704,534, filed Feb. 8, 2007, eight pages.

Non-Final Office Action mailed on Mar. 31, 2009, for U.S. Appl. No. 11/704,534, filed Feb. 8, 2007, twenty-seven pages.

Non-Final Office Action mailed on Feb. 25, 2010, for U.S. Appl. No. 11/704,534, filed Feb. 8, 2007, ten pages.

\* cited by examiner

DRUG ELUTING LEAD SYSTEMS

TECHNICAL FIELD

The methods and devices described herein relate generally to the field of medical electrical lead systems. More specifically, the methods and devices described herein relate to medical electrical lead systems for treatment of neural tissue, such as brain tissue, where the lead systems include at least one bioactive agent and/or are configured to provide a therapeutic effect to the neural tissue. The methods and devices described herein may have particular utility in the area of treatment of neurological disorders.

BACKGROUND

Neurological disorders are prevalent in the United States and around the rest of the world, with millions of people suffering from various types of neurological disorders of varying severity. A person who has a neurological disorder may be substantially debilitated, and may experience a significant decline in quality of life.

One example of a neurological disorder is epilepsy, which is characterized by the occurrence of seizures. Because epilepsy is characterized by seizures, its sufferers can be limited in the kinds of activities in which they may participate. For example, an epileptic may have limited or no ability to drive, work, or participate in recreational activities. Some epilepsy sufferers have serious seizures with such high frequency that they are effectively incapacitated. Additionally, in some cases, epilepsy is progressive, and can be associated with degenerative disorders and conditions. Over time, epileptic seizures may become more frequent and serious, and in particularly severe cases, may lead to the deterioration of other brain functions, as well as physical impairment.

Drug therapy and surgery are examples of current methods that may be used to treat epilepsy. Various antiepileptic drugs are available, and may be administered, for example, at the onset of pre-seizure symptoms or auras, to mitigate the effects of epilepsy. Surgical procedures include radical surgical resections, such as hemispherectomies, corticectomies, lobectomies and partial lobectomies, as well as less radical procedures, including lesionectomies, transections, and stereotactic ablation. An additional procedure that may be used to treat epilepsy is electrical stimulation, in which seizures may be treated and/or terminated by applying electrical stimulation to the brain. Typically, the detection and responsive treatment of seizures via electrical stimulation can include analysis of electroencephalogram (EEG) waveforms and electrocorticogram (ECoG) waveforms. An EEG waveform includes signals representing aggregate neuronal activity potentials detectable via electrodes applied to a patient's scalp, and/or signals obtained from deep in a patient's brain via depth electrodes and the like. An ECoG waveform includes signals obtained from internal electrodes near the cortex of the brain (generally on or under the dura mater), and/or brain signals from deeper structures.

Generally, it is preferable to detect and treat a seizure at or near its inception, or even before it has begun. The beginning of a seizure, or an onset, may be a clinical onset or an electrographic onset. A clinical onset represents the beginning of a seizure as manifested through observable clinical symptoms, such as involuntary muscle movements or neurophysiological effects such as lack of responsiveness. An electrographic onset, which typically occurs before a clinical onset and which may enable intervention before the patient suffers symptoms, refers to the beginning of detectable electrographic activity indicative of a seizure.

Epilepsy is only one example of a neurological disorder. Additional examples of neurological disorders include movement disorders (e.g., Parkinson's disease), psychiatric disorders, sleep disorders, and language disorders. As briefly discussed above, these and other neurological disorders can severely disrupt a person's quality of life. Thus, it would be preferable to provide devices and methods that may be used to provide drugs and/or other bioactive agents to a target site to treat a neurological disorder.

BRIEF SUMMARY

Described here are medical electrical lead systems for treatment of neurological disorders, as well as related methods. The lead systems may be configured to be at least partially implanted in a body of a subject. For example, the lead systems may be configured to be at least partially implanted into neural tissue, such as brain tissue. The lead systems may be used to release one or more bioactive agents, such as therapeutic agents, into the body of the subject. These bioactive agents may be released in conjunction with the application of other treatment methods, such as electrostimulation, or may be released independently of any other treatment methods.

The lead systems generally comprise a lead body, an electrode that is connected to the lead body, and at least one bioactive agent. The electrode and/or lead body comprises a substrate, and the bioactive agent is supported by the substrate. In some variations, the bioactive agent may be supported by a substantial portion of the area of the substrate.

The methods include methods of using lead systems. Some variations of the methods comprise at least partially implanting a lead system in neural tissue of a subject, such as a brain of a subject. In certain variations, the lead system comprises a lead body, an electrode connected to the lead body, and at least one bioactive agent. The electrode and/or lead body comprises a substrate, and the bioactive agent is supported by the substrate. In some variations, the bioactive agent may be supported by a substantial portion of the area of the substrate. In certain variations in which the lead system is at least partially implanted in neural tissue, the result may be the formation of at least one microlesion in the neural tissue. In such variations, at least one of the lead body and the electrode may include a bioactive agent that is adapted to inhibit neuronal regeneration and/or neuronal reconnection. Alternatively, a bioactive agent that is adapted to encourage glial proliferation and/or healing of microlesions may be used in the lead systems for certain applications.

A lead system may include just one bioactive agent or multiple bioactive agents. In some variations, a lead system may include a substrate and a bioactive agent that contacts the substrate, such as a bioactive agent that is in the form of a coating on the substrate. The bioactive agent may comprise an antiproliferative agent, a bactericidal agent, a bacteriostatic agent, an antiepileptic agent, an antifungal agent, or any other appropriate bioactive agent. Examples of antiproliferative agents that may be used as bioactive agents here include antiproliferative agents that are capable of limiting or preventing glial encapsulation (e.g., of a lead body and/or an electrode), as well as other types of antiproliferative agents. Specific examples of antiproliferative agents include bone morphogenic proteins, ciliary neurotrophic factor, ribavirin, sirolimus, mycophenolate, mofetil, azathioprine, paclitaxel, and cyclophosphamide. Examples of bactericidal and/or bacteriostatic agents that may be used in the lead systems described herein include quinolone, fluoroquinolone, betalactam, aminoglycoside, penicillin, macrolide, monobactam, lincosamide, tetracycline, cephalosporin, lipopeptide, streptogramin, carbapenem, sulfonamide, aminoglycoside, oxalodinone, nitrofuran, ketolide, glycylcycline families of antibiotics, and silver ions. Examples of antiepileptic agents that may be used in the lead systems include acetazolamide, carbamazepine, clonazepam, clorazepate, diazepam, divalproex, ethosuximide, ethotoin, felbamate, fosphenytoin, gabapentin, lamotrigine, levetiracetam, mephobarbital, methsuximide, oxcarbazepine, phenacemide, phenobarbital, phenytoin, pregabalin, primidone, thiopental, tiagabine, topiramate, trimethadione, valproate, zonisamide, and tetrodotoxin. Additionally, examples of antifungal agents that may be appropriate for use in the lead systems include amphotericin B, anidulafungin, butenafine, butoconazole, caspofungin, ciclopirox, clioquinol, econazole, fluconazole, flucytosine, griseofulvin, traconazole, ketoconazole, micafungin, miconazole, naftifine, natamycin, nystatin, oxiconazole, sulconazole, sulfanilamide, terbinafine, terconazole, undecylenic, and voriconazole. Other types of bioactive agents may also be used.

In certain variations, the lead systems may include a substrate, a bioactive agent, and a material that is supported by the substrate and that is different from the bioactive agent. The bioactive agent may be encapsulated within the material, or the material may be in the form of a layer over the bioactive agent. In some variations, the bioactive agent may be in the form of a layer over the material. The material may be, for example, silicone or a hydrogel. In variations in which the material is silicone, the density of the silicone can be manipulated to modulate the elution characteristics of the silicone. As the elution characteristics of the silicone change, the rate of bioactive agent release from the silicone also can change.

In certain variations, the material may be bioerodible. In other words, the material may be bioabsorbable, such that the body absorbs the material, and/or biodegradable, such that the body degrades and eventually excretes the material. For example, the material may comprise a bioerodible polyanhydride or polyanhydride compound. Examples of bioerodible polyanhydrides and polyanhydride compounds include fatty acid-terminated polyanhydrides, poly(fatty acid dimer), copolymers of poly(sebacic acid) and fatty acid, and copolymers of dimer fatty acids. Specific examples of bioerodible polyanhydrides and polyanhydride compounds include poly [1,3-bis(carboxyphenoxy)propane-co-sebacic-acid], poly (fumaric acid), poly(sebacic acid), poly(erucic acid dimer), copolymers of fumaric acid and sebacic acid, poly(sebacic-co-ricinoleic acid maleate), poly(sebacic-co-ricinoleic acid succinate), and poly(sebacic-co-12-hydroxystearic acid succinate).

Some variations of the lead systems may include at least one polymer, such as a bioerodible polymer, that is supported by the substrate. Examples of polymers that may be included in the lead systems include poly(3,4-ethylenedioxythiopene) (PEDOT) and poly(3,4-ethylenedioxythiopene) poly(styrenesulfonate) (PEDOT:PSS). In certain variations, the bioactive agent may be dispersed throughout, and/or encapsulated within, the polymer. In some variations, the polymer may be in the form of a layer over the bioactive agent. In certain variations, the bioactive agent may be in the form of a layer over the polymer.

A lead system may include just one electrode or a plurality of electrodes (e.g., two, three, four, five, six, eight, or ten electrodes) that are connected to its lead body. Some variations of lead systems may include at least two electrodes, each of which comprises a substrate supporting a bioactive agent. The substrates of the electrodes may be formed of the same or different materials, and the bioactive agents may be the same as each other or different from each other.

Some of the methods described here are methods of making lead systems. Certain variations of these methods comprise coating an electrode and/or a lead body of a medical electrical lead system with at least one bioactive agent, where the electrode and the lead body are connected to each other. Some variations of the methods may comprise coating a substantial portion of the area of the electrode and/or lead body with the bioactive agent. Certain variations of the lead systems may be configured to release at least one bioactive agent when the lead systems are at least partially implanted in neural tissue of a subject. In some variations in which a lead system includes both a bioactive agent and a bioerodible material that is different from the bioactive agent, erosion of the bioerodible material, when the lead system is at least partially implanted in neural tissue of a subject, may result in the release of the bioactive agent into the neural tissue of the subject. Coating methods that may be used in the methods described herein include vapor deposition (e.g., physical vapor deposition), ionic plasma deposition, spraying, and/or dipping, as well as other methods.

DETAILED DESCRIPTION

Described here are devices and related methods for treating neurological disorders with one or more bioactive agents. The devices generally are medical electrical lead systems including a lead body and at least one electrode that is connected to the lead body. The lead systems can further include at least one bioactive agent, and/or can be configured to provide a therapeutic effect to neural tissue in the central and/or peripheral nervous systems. In some variations of the lead systems, at least one of the electrode and the lead body comprises a substrate that supports a bioactive agent. For example, the bioactive agent may be in the form of a coating on the substrate. In such variations, the lead systems may be used to deliver the bioactive agent to a target site, such as neural tissue (e.g., brain tissue). The bioactive agent may be dispersed throughout, and/or encapsulated by, one or more other materials on the substrate, such as a polymer coating. The lead systems may be configured to provide a continuous supply of bioactive agent to a target site over a period of time. Furthermore, the lead systems may be connected to one or more implantable medical devices, such as electrostimulation and/or recording devices, which allow the lead systems to provide other treatments in addition to the bioactive agent treatment.

Figure 1:
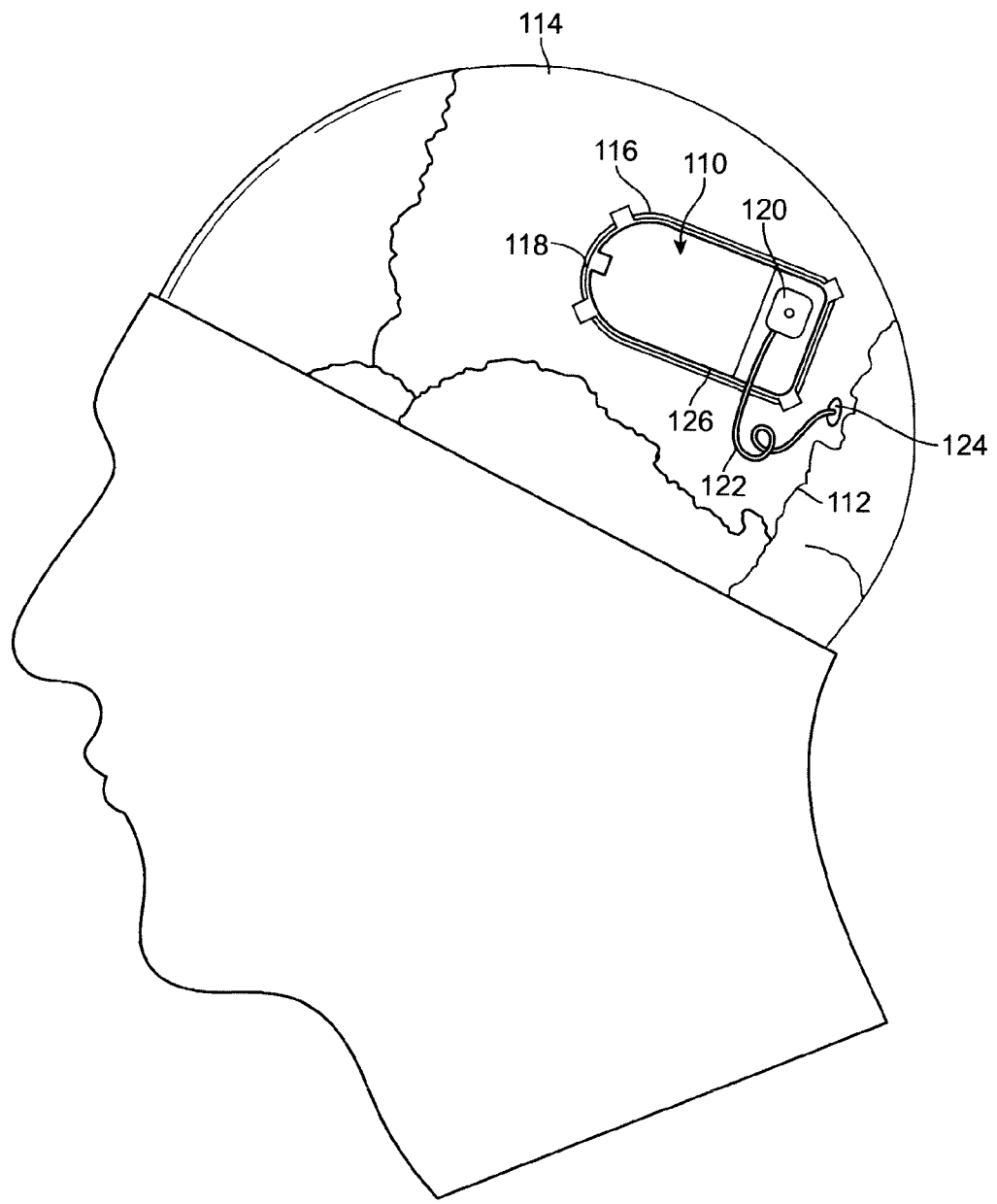
FIG. 1 is an illustration of a cranium of a subject, showing an implantable neurostimulation device as implanted, and a medical electrical lead system connected to the implantable neurostimulation device and extending to the brain of the subject.

Turning now to the figures, FIG. 1 shows an implantable medical device (110), such as an electrostimulation device, affixed to a cranium (114) of a subject by way of a ferrule (116). Ferrule (116) is a structural member that is adapted to fit into a cranial opening, attach to the cranium, and retain device (110). One example of a method that may be used to implant device (110) and affix it to cranium (114) includes performing a craniotomy in the parietal bone (not shown) anterior to the lamboid suture (112) to define an opening (118) slightly larger than device (110). Ferrule (116) is then inserted into opening (118) and affixed to cranium (114). Thereafter, device (110) is inserted into, and affixed to, ferrule (116). The presence of ferrule (116) may, for example, help to ensure that device (110) is tightly and securely implanted.

As shown in FIG. 1, device (110) includes an outer housing (126), and a lead connector (120) configured to receive one or more electrical lead systems. Housing (126) may provide protection to the components of device (110), and may be formed of, for example, one or more metals, such as titanium. Additionally, housing (126) may enclose a battery and any electronic circuitry that may be required or desired to provide device (110) with its functionality. In some variations, a telemetry coil may be located in the interior of device (110), or may be provided outside of housing (126) and integrated with lead connector (120), to facilitate communication between device (110) and external devices.

Figure 2:
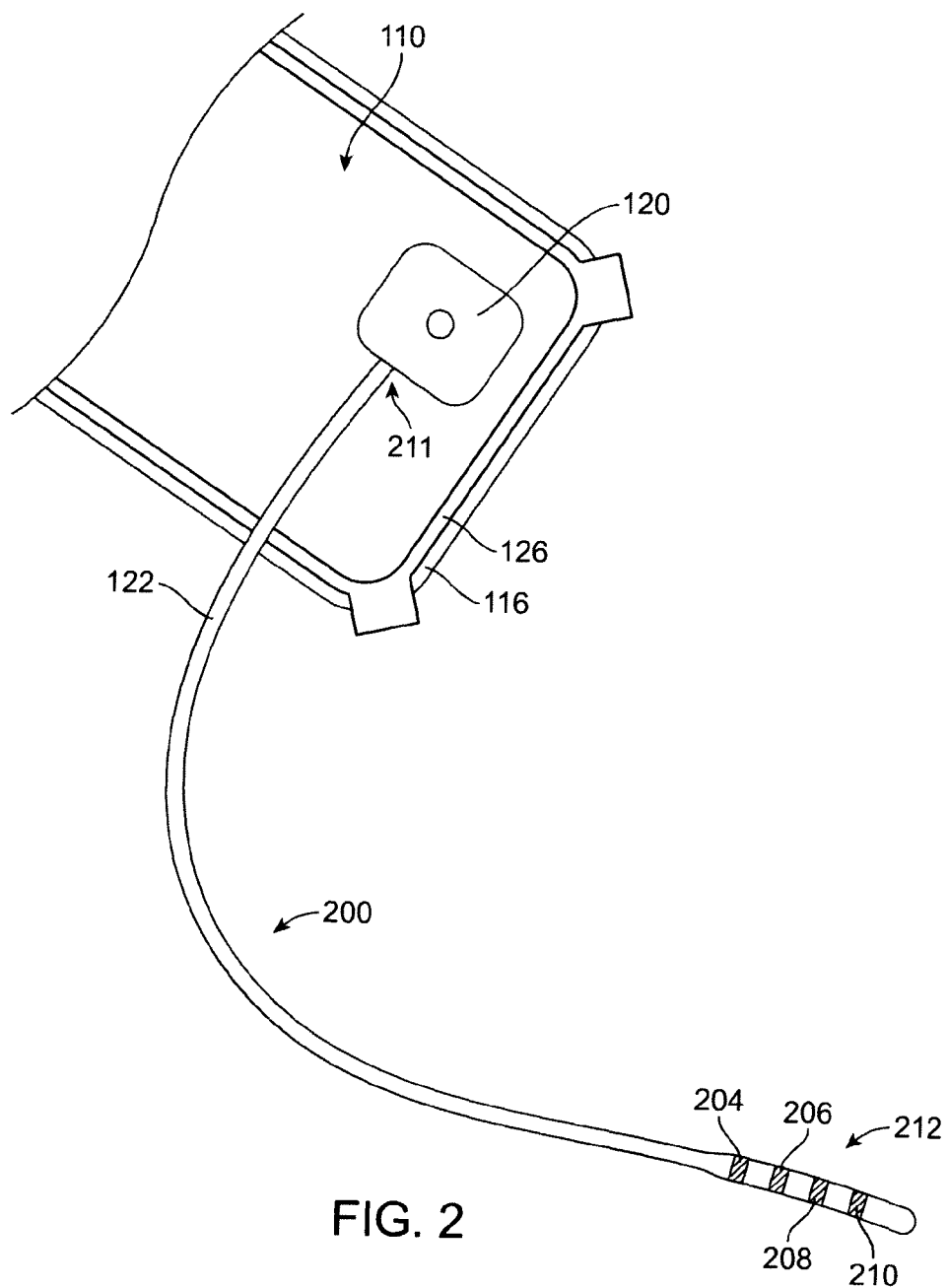
FIG. 2 is a partial top view of the device and lead system of FIG. 1.

In FIG. 1, lead connector (120) is connected to a lead body (122) of a medical electrical lead system (200) (shown in FIG. 2). Lead body (122) extends through a burr hole (124) or other opening in cranium (114). Though not shown, in FIG. 2, the portion of lead body (122) that extends past burr hole (124) is coupled to four electrodes that are implanted into a desired location in the subject's brain. If the length of lead body (122) is substantially greater than the distance between device (110) and burr hole (124), then any excess may be urged into a configuration, such as an uncoiled configuration, that consolidates the excess lead body (e.g., under the scalp). In some variations, burr hole (124) may be sealed after implantation to limit or prevent further movement by lead system (200). This sealing may be provided, for example, by affixing a burr hole cover apparatus to cranium (114) at least partially within burr hole (124). Burr hole sealing is described, for example, in U.S. Pat. No. 6,006,124, which is hereby incorporated by reference in its entirety.

Lead connector (120) helps to secure lead body (122) to device (110). Lead connector (120) also facilitates electrical connection between circuitry within device (110) and one or more conductors in lead body (122). The conductors, in turn, are coupled to the electrodes. Lead connector (120) may accomplish the above-described functions in a substantially fluid-tight environment and in a biocompatible manner.

In general, device (110) may be used to treat one or more neurological disorders. For example, device (110) may treat epilepsy by detecting epileptiform activity or an electrographic seizure from the brain, and applying neurostimulation to the brain. A device such as device (110) may be able to both sense epileptiform activity, and provide electrical stimulation to the brain in response. However, in some variations, separate devices may be used for monitoring brain activity and applying electrical stimulation or neurostimulation. Brain activity may be detected, for example, by comparing ongoing activity to typical epileptiform activity, including identifying characteristics of epileptiform activity or an electrographic seizure from ongoing brain activity. Once activity is detected, stimulation may be applied to the affected region. Additional stimulation to secondary brain regions may also be applied.

As described above, device (110) may be an electrostimulation device or neurostimulation device. Neurostimulation devices are described, for example, in U.S. Patent Application Publication No. US 2006/0058856 and U.S. patent application Ser. No. 11/525,586, both of which are hereby incorporated by reference in their entirety. Other examples of implantable medical devices include recording devices. Moreover, in some variations, an implantable medical device may be configured to detect and/or respond to neurological activity other than epileptiform activity. Non-limiting examples of such neurological activity include activity associated with movement disorders, psychiatric disorders, sleep disorders, language disorders, migraine headaches, and/or chronic pain. While an implantable medical device such as device (110) may have a therapeutic function, some or all of the actions performed by a medical device used in conjunction with a lead system may not be therapeutic. For example, the actions may involve data recording or transmission, providing warnings to the subject, or any of a number of alternative actions. In some variations, a neurostimulation device may not be a single device, but may be a system of component devices. Thus, a neurostimulation device may also function as a diagnostic device, and may be interfaced with external equipment.

While device (110) is shown as being affixed to cranium (114), devices may be positioned in any of a number of different places either within or outside of a body of a subject. For example, in some variations, a device may be implanted under a subject's scalp, but external to the subject's cranium. In certain variations (e.g., when it is not possible to implant a device intracranially), a device may be implanted pectorally, with leads extending through the subject's neck and between the subject's cranium and scalp, as necessary. Any other suitable positions for a device may also be used.

FIG. 2 shows an enlarged view of a portion of device (110), as well as lead system (200) including the lead body (122) shown in FIG. 1. As shown in FIG. 2, in addition to including lead body (122), which has a proximal end (211) and a distal end (212), lead system (200) also includes multiple cylindrical electrodes (204), (206), (208), and (210). Electrodes (204), (206), (208), and (210) are located at distal end (212) of lead body (122), and are connected to conductors (not shown) embedded within the lead body. The connection between the electrodes and the conductors allows electrical stimulation to be transmitted from device (110) to the brain of the subject. The electrodes of lead system (200) may be configured, for example, to sense brain activity, to apply neurostimulation, and/or to record brain signals.

Figure 3A:
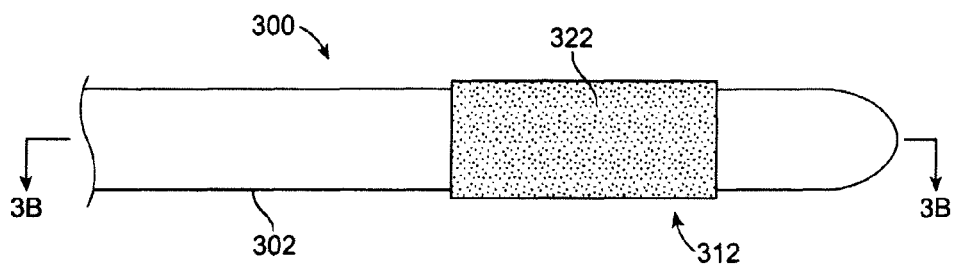
FIG. 3A is a side view of a portion of a medical electrical lead system.
Figure 3B:
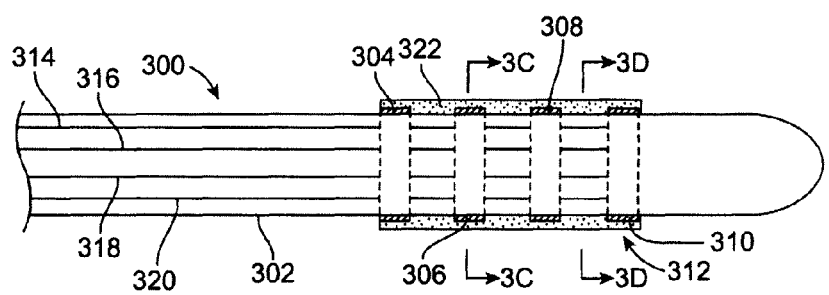
FIG. 3B is a cross-sectional view of the portion of the lead system of FIG. 3A, taken along line 3B-3B.
Figure 3C:
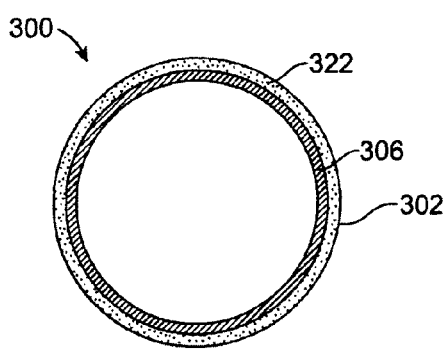
FIG. 3C is a cross-sectional view of the portion of the lead system of FIG. 3B, taken along line 3C-3C.
Figure 3D:
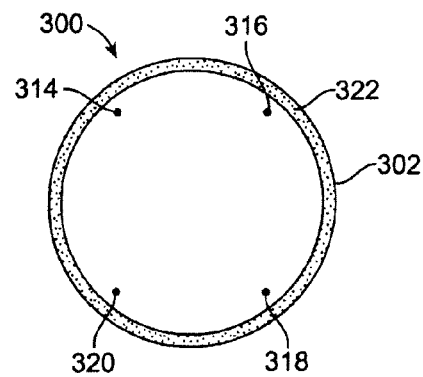
FIG. 3D is a cross-sectional view of the portion of the lead system of FIG. 3B, taken along line 3D-3D.

FIGS. 3A-3D show a distal portion of another variation of a medical electrical lead system. As shown there, a medical electrical lead system (300) includes a lead body (302) and multiple cylindrical electrodes (304), (306), (308), and (310) that are connected to the lead body at its distal end (312). Four conductors (314), (316), (318), and (320) (the positioning of which is shown in FIG. 3D) are embedded within lead body (302) and are connected to the electrodes. The conductors provide electrical connection between the electrodes and circuitry within a device that is connected to the lead system during use, such as an implantable electrostimulation device. While electrodes (304), (306), (308), and (310) are shown as being ring-shaped, electrodes having other shapes, such as disc-shaped electrodes, may alternatively or additionally be used in lead systems. Lead system (300) further includes a coating (322) over the cylindrical electrodes and portions of the lead body. Coating (322) includes one or more bioactive agents. During use of lead system (300), the bioactive agents in coating (322) may be released into the body of the subject and may, for example, provide a therapeutic effect.

A coating such as coating (322) may be formed of any of a number of different biocompatible materials. In some variations, a coating on a lead system may be formed simply of one or more bioactive agents. In certain variations, a coating on a lead system may include one or more bioactive agents in combination with one or more other materials, such as silicone. The bioactive agents may, for example, be dispersed throughout, or encapsulated by, the other materials. Moreover, in some variations, the other materials may form one or more coatings over the bioactive agents, and/or the bioactive agents may form one or more coatings over the other materials.

Examples of other materials that may be used in a coating on a lead system include polymers, such as electrically conductive polymers. In variations in which a coating includes one or more electrically conductive polymers, the electrically conductive polymers may enhance the electrical connection between a target site in the body of a subject, and the electrodes and conductors of the lead system. Examples of polymers that may be included in a coating on a lead system include poly(3,4-ethylenedioxythiopene) and poly(3,4-ethylenedioxythiopene) poly(styrenesulfonate). Other polymers may also be appropriate.

In certain variations, one or more bioerodible materials may be used in a coating on a lead system. As the bioerodible materials erode in the body, they may provide controlled release of a bioactive agent or agents. Examples of bioerodible materials include bioerodible polyanhydrides and polyanhydride compounds. Examples of bioerodible polyanhydrides and polyanhydride compounds include fatty acid-terminated polyanhydrides, poly(fatty acid dimer), copolymers of poly(sebacic acid) and fatty acid, and copolymers of dimer fatty acids. Specific examples of bioerodible polyanhydrides and polyanhydride compounds include poly [1,3-bis(carboxyphenoxy)propane-co-sebacic-acid], poly (fumaric acid), poly(sebacic acid), poly(erucic acid dimer), copolymers of fumaric acid and sebacic acid, poly(sebacic-co-ricinoleic acid maleate), poly(sebacic-co-ricinoleic acid succinate), and poly(sebacic-co-12-hydroxystearic acid succinate).

Further examples of materials that may be used in a coating include porous materials, such as hydrogels. The materials may, for example, have a pore volume percent of from about 10 to about 100 nanometers. Such porous materials may be used to deliver one or more bioactive agents to a target site over a sustained period of time. For example, a bioactive agent may elute from a hydrogel coating over a period of about one to ten days. Other bioerodible materials or non-bioerodible materials may alternatively or additionally be used, as deemed appropriate.

While a lead system with one coating has been described, lead systems may have multiple coatings, such as two, three, four, five, or ten coatings. Some or all of the coatings may include the same materials and/or bioactive agents, or some or all of the coatings may include different materials and/or bioactive agents. The bioactive agent or agents that are used in a particular coating may be selected, for example, based on the anticipated position of that coating once the lead system has been implanted at a target site. Lead systems may include lead bodies and/or electrodes that are entirely coated, or may include lead bodies and/or electrodes having coated regions and uncoated regions. Moreover, a lead system may include just one coating layer, or may include multiple layers of coatings.

The bioactive agents that are delivered to a target site from a lead system may be any of a number of different types of bioactive agents, depending on the disorder or disorders which are desired to be treated.

As an example, for treatment of epilepsy, one or more of the bioactive agents typically would include an antiepileptic agent. Examples of antiepileptic agents include acetazolamide, carbamazepine, clonazepam, clorazepate, benzodiazepine derivatives (e.g., diazepam), divalproex, ethosuximide, ethotoin, felbamate, fosphenytoin, gabapentin, lamotrigine, levetiracetam, mephobarbital, methsuximide, oxcarbazepine, phenacemide, phenobarbital, phenytoin, pregabalin, primidone, thiopental, tiagabine, topiramate, trimethadione, valproate, vigabatrin, zonisamide, tetrodotoxin, allopregnanolone, and ganaxolone.

Additional examples of bioactive agents include antiproliferative agents, bactericidal agents, bacteriostatic agents, antifungal agents, etc.

Examples of antiproliferative agents include antiproliferative agents that are capable of limiting or preventing glial encapsulation of the substrates on which the antiproliferative agents are coated. For example, the antiproliferative agents may be used to limit or prevent glial encapsulation of at least one of the lead body and the electrode or electrodes of a lead system. Limitation of glial activity and/or proliferation may, for example, enhance electrical connectivity between electrodes and neural tissue in which the electrodes are implanted. Other types of antiproliferative agents may also be used. Specific examples of antiproliferative agents include bone morphogenic proteins (BMPs), ciliary neurotrophic factor (CNF), ribavirin, sirolimus (also known as rapamycin), mycophenolate, mofetil, azathioprine, paclitaxel, and cyclophosphamide.

Bactericidal and/or bacteriostatic agents, as well as antifungal agents, may be used, for example, to limit post-operative risk of infection. Examples of bactericidal and/or bacteriostatic agents include quinolone, fluoroquinolone, beta-lactam, aminoglycoside, penicillin, macrolide, monobactam, lincosamide, tetracycline, cephalosporin, lipopeptide, streptogramin, carbapenem, sulfonamide, aminoglycoside, oxalodinone, nitrofuran, ketolide, glycylcycline families of antibiotics, and silver ions. Examples of antifungal agents include amphotericin B, anidulafungin, butenafine, butoconazole, caspofungin, ciclopirox, clioquinol, econazole, fluconazole, flucytosine, griseofulvin, traconazole, ketoconazole, micafungin, miconazole, naftifine, natamycin, nystatin, oxiconazole, sulconazole, sulfanilamide, terbinafine, terconazole, undecylenic, and voriconazole.

Other examples of bioactive agents include benzodiazapenes and barbiturates. In some variations, cancer drugs such as antineoplastics may be used as bioactive agents (e.g., to inhibit cellular proliferation). In certain variations, the bioactive agents that are used in a lead system may be adapted to promote neural adhesion. For example, the bioactive agents may be cell adhesion molecules. Other examples of bioactive agents include plasmids, linear DNA or RNA fragments, other DNA- or RNA-based molecules, and growth factors. These bioactive agents may be used, for example, to induce a desired neural, glial, and/or immune response. Still further examples of bioactive agents include cells, such as living cells that have been biologically manipulated, engineered cells, and cells of a particular phenotype. For example, a lead system may include a layer of cells. The types of cells that are used can be selected based on the desired effect. In some cases, electrical stimulation may be used to cause the cells to release desired neurotransmitters. Additional examples of bioactive agents include neurotrophic factors and neuropeptides, proteins exhibiting bioactive activity, glycans, and enzymes (e.g., enzymes that help metabolize glutamate).

Moreover, while certain bioactive agents described herein have been described as treating certain disorders, the bioactive agents described herein may be able to treat more than one type of disorder or condition. As an example, tetrodotoxin may be used to treat disorders other than epilepsy. Generally, the bioactive agents described herein may be employed when they can provide any function that is desirable and/or useful.

Still further examples of bioactive agents that may be used include bioactive agents that treat motor disorders (e.g., Parkinson's disease, dystonia, or tremors such as essential tremor), psychiatric disorders (e.g., bipolar disorder or depression, such as major depression disorder), language disorders, sleep disorders, and Tourette's syndrome. These are merely examples of different types of bioactive agents. Any other bioactive agents suitable for treating neurological disorders or other disorders of the body, or for providing other benefits, such as preventive care, may be used with the lead systems described herein as appropriate. For example, in some variations, bioactive agents having anti-inflammatory properties, such as steroids, may be used. Anti-inflammatory agents may advantageously limit the extent of inflammation resulting from, for example, the process of implanting electrodes into and/or upon neural tissue. The process of implantation may include mechanically and chemically manipulating the neural tissue in such a way as to cause inflammation which, in turn, may produce edema and swelling. As a result, the time for application of needed therapy may be delayed. Accordingly, providing one or more anti-inflammatory agents to the neural tissue may be desirable.

In certain variations, bioactive agents that may typically exhibit central nervous system (CNS) or systemic side effects, difficult deliverability, and/or unfavorable pharmacokinetics may be used with the lead systems described herein (e.g., because the lead systems may deliver the bioactive agents directly to a target location relatively efficiently).

Some bioactive agents may be used to facilitate neurostimulation. The bioactive agents may be delivered to neural tissue in conjunction with, prior to, and/or after, neurostimulation of the neural tissue. Examples of bioactive agents that may be used to facilitate neurostimulation include carbamazepine, oxcarbazepine, and phenytoin. These bioactive agents may inhibit rapid firing, and may preferentially encourage a depolarization-block response to high-frequency neurostimulation (rather than a neural-firing response). Additional examples of bioactive agents that may be used to facilitate neurostimulation include glutamate-blocking agents such as lamotrigine and topiramate. These glutamate-blocking agents may diminish excitatory effects of neurostimulation. Further examples of bioactive agents that may be used to facilitate neurostimulation include GABAergic agents, such as topiramate, allopregnanolone, ganaxolone, benzodiazepines, barbiturates, tiagabine, or other agents which potentiate inhibition and which may be expected to potentiate inhibitory effects of neurostimulation.

Certain bioactive agents may be adapted to facilitate the recording of one or more signals from a brain of a subject, and thus may be used to enhance a recording procedure. These bioactive agents may also be delivered to neural tissue in conjunction with, prior to, and/or after, recording. Examples of bioactive agents that may facilitate recording (and that may also facilitate neurostimulation) include agents that limit or prevent an inflammatory response, and thereby also limit or prevent undesirable physical changes to the electrode-tissue interface. Examples of such bioactive agents include anti-inflammatory agents, antiproliferative agents (e.g., bone morphogenic proteins, ciliary neurotrophic factor, ribavirin, sirolimus, mycophenolate, mofetil, azathioprine, paclitaxel, and cyclophosphamide), and anti-gliotic agents. In some variations, one or more bioactive agents that facilitate brain signal recording may be delivered to neural tissue over a relatively long period of time, and may have a cumulative effect on the neural tissue.

In some variations, a lead system may include one or more bioactive agents that are adapted to inhibit neuronal regeneration and/or neuronal reconnection. When the lead system is at least partially implanted into neural tissue, it may form at least one microlesion in the neural tissue. The bioactive agents may be used to at least temporarily maintain that microlesion. It is believed that, in some instances and/or under certain circumstances, microlesions may result in a decreased occurrence of seizures. Thus, it may be desirable in some cases to purposefully maintain microlesions in neural tissue. By contrast, in certain cases, it may be desirable to enhance the healing of microlesions, as they may result in post-traumatic epileptiform activity. By using bioactive agents that hasten the healing of microlesions, the occurrence of seizures shortly after surgery may be limited.

Electrodes such as electrodes (304), (306), (308), and (310) described above may be configured, for example, to sense brain activity, to apply neurostimulation, and/or to record brain signals. Electrodes may be formed of any of a number of different materials. Examples of electrode materials include titanium, platinum, platinum alloyed with iridium, titanium nitride, iridium oxide, no nickel stainless steels, conductive organic materials (e.g., solid carbon), silicon, and/or any other materials and combinations of materials that are known to be suitable for use in electrodes. In certain variations, an electrode may be a semiconductor electrode. Furthermore, in some variations, a lead system may include one or more optical electrodes, or optodes, that are configured to optically measure signals. In such variations, the optodes may also be used to monitor bioactive agent levels at a target site. In certain variations, an electrode may be formed of one or more sintered metal materials, and may serve as a reservoir for a bioactive agent. The bioactive agent may be released from the reservoir through pores or holes in the sintered metal materials. In some variations, the sintered electrode may be back-filled with a material, such as a hydrogel or a rubber, that is compounded with one or more bioactive agents. The bioactive agents may then be released from the hydrogel or rubber and through pores or holes in the sintered metal materials.

Referring back to FIG. 2, electrodes (204), (206), (208), and (210) are located at distal end (212) of lead body (122). However, some variations of lead systems may alternatively or additionally include one or more electrodes that are located proximal to the distal end of the lead body. The locations of the electrodes of a lead system may be selected based on, for example, the characteristics of the target site.

A lead body such as lead body (122) may be formed of any of a number of different materials. In certain variations, a lead body may be substantially formed of one or more insulating materials. In some variations, a lead body may be formed of one or more polymers, such as polyurethanes, polytetrafluoroethylene, polyesters, and polyamides (e.g., nylon). In certain variations, a lead body may be formed of silicone.

While lead systems including four conductive wires have been shown, lead systems may include any number of conductive wires, such as one, two, three, four, five, or ten conductive wires. One or more of the wires may extend straight through the side wall of a lead body, and/or may wind or coil within the lead body. In some variations, the conductive wires themselves may be coated or sheathed within a non-conductive and/or protective material, such as silicone, polyurethane, or polyethylene.

In certain variations, the dimensions of a lead system may be selected to provide the lead system with a relatively low profile. This low profile may prevent the lead system from being easily visible from the outside when the lead system is implanted within a subject's head (e.g., so that the lead system does not form a protrusion on the subject's head). Such lead systems may, for example, include one or more relatively thin coatings, the thinness of which generally will depend on the particular type of coating that is used. For example, if the coating is formed from titanium nitride (TiN), iridium oxide (IrOx), or platinum iridium (PtIr), the thinness of the coating may be on the order of three to twenty microns.

Figure 4:
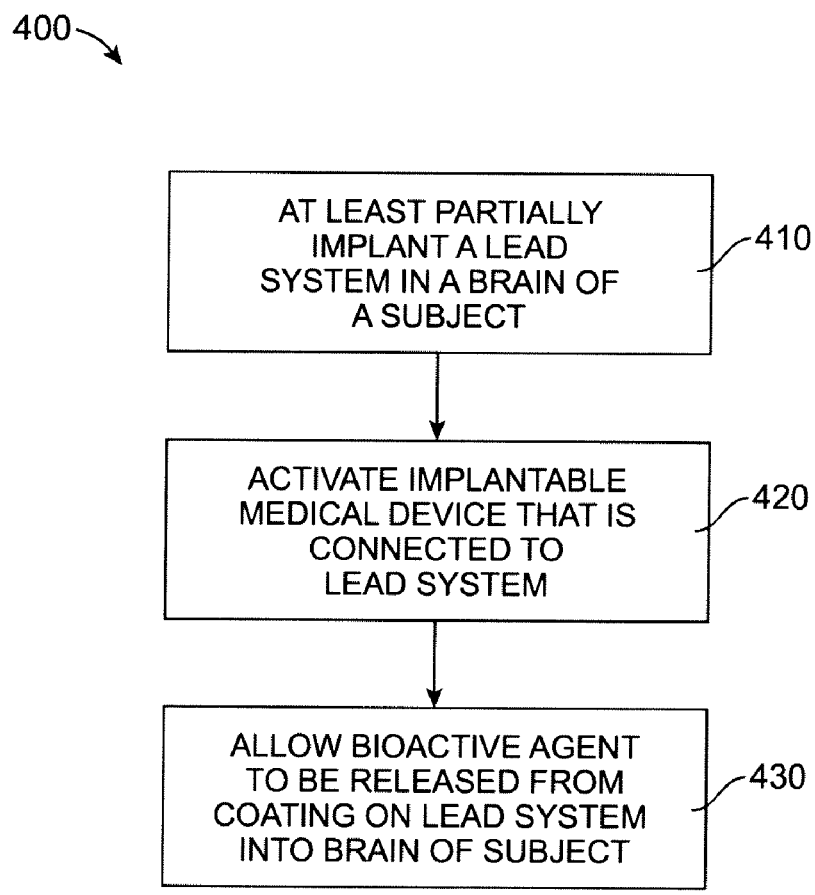
FIG. 4 is a flowchart representation of a method of using a lead system in a body of a subject.

Various methods may be employed to deliver one or more bioactive agents to a target site within a body of a subject, using one of the lead systems described herein. FIG. 4 provides a flowchart representation of one variation of such a method (400). As shown there, method (400) includes at least partially implanting a lead system in a brain of a subject (410). The lead system includes a lead body, at least one electrode, and a coating including at least one bioactive agent. The lead system also is connected to an implantable medical device. The lead system may be entirely implanted in the brain of the subject, or at least one of its components may be located outside of the brain of the subject. The implantable medical device may be partially or entirely implanted into the head of the subject, such as intracranially in the subject's parietal bone, in a location anterior to the lambdoid suture (as described, for example, with reference to FIG. 1 above).

After the lead system has been at least partially implanted in the brain of the subject, the medical device is activated (420). The medical device may be configured, for example, to sense brain activity, such as epileptic activity. Method (400) further includes allowing bioactive agent to be released from the coating on the lead system and out into the brain of the subject (430). The bioactive agent may be released over a relatively short period of time or over a relatively long period of time, depending on the intended or desired effect of the agent and/or on the particular characteristics or properties of the agent being used. For some intended effects with some agents, a relatively short period of time may be one day. For other intended effects with other agents, a relatively long period of time may be ten days. Another method that might be used to deliver one or more bioactive agents to a target site within a body of a subject, using one of the lead systems described herein, include the application of electroporation to cause a desired effect or effects with the agents.

Figure 5A:
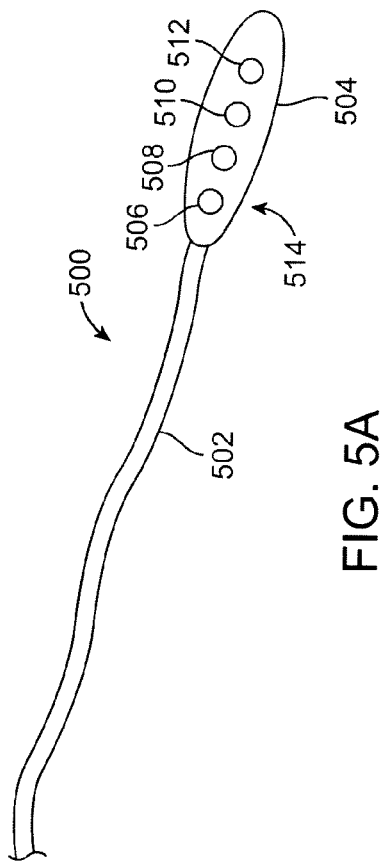
FIG. 5A is a top view of a portion of a medical electrical lead system.
Figure 5B:
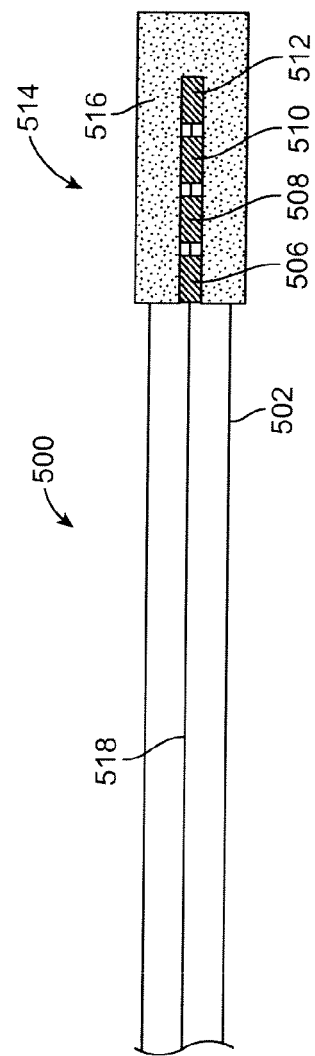
FIG. 5B is a side cross-sectional view of the lead system of FIG. 5A.

While a lead system comprising a depth lead has been described with reference to FIGS. 2 and 3A-3D above, other types of lead systems, such as branched depth electrodes and two-dimensional electrode arrays, may include one or more bioactive agents. For example, and referring to FIGS. 5A and 5B, a lead system (500) includes a lead body (502) and an enlarged end portion (504) at the distal end (514) of the lead system. Enlarged end portion (504) includes four disc electrodes (506), (508), (510), and (512) encapsulated in a coating (516). Coating (516) includes one or more bioactive agents that may be released into a target site when lead system (500) is being used. A conductor (518) is embedded within lead body (502) and runs along the length of the lead body, electrically connecting the electrodes to a medical device. Lead system (500) is a cortical strip lead, and may, for example, be positioned on a surface of brain tissue during use.

Lead systems that are directly connected to neurostimulation devices have been described here. However, in certain variations, a lead system may be indirectly connected to an implantable medical device. For example, a lead system may be wirelessly connected to an implantable medical device.

While the methods and devices have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the appended claims.

What is claimed is:

1. A medical electrical lead system configured to be at least partially implanted in neural tissue of a subject, comprising:
   a lead body;
   an electrode connected to the lead body and comprising a substrate; and
   at least one antiepileptic agent supported by a substantial portion of the area of the substrate of the electrode.

2. The lead system of claim 1, wherein the lead system is configured to be at least partially implanted in a brain of a subject.

3. The lead system of claim 1, wherein the lead system comprises a plurality of electrodes that are connected to the lead body.

4. The lead system of claim 1, wherein the at least one antiepileptic agent is selected from the group consisting of acetazolamide, carbamazepine, clonazepam, clorazepate, diazepam, divalproex, ethosuximide, ethotoin, felbamate, fosphenytoin, gabapentin, lamotrigine, levetiracetam, mephobarbital, methsuximide, oxcarbazepine, phenacemide, phenobarbital, phenytoin, pregabalin, primidone, thiopental, tiagabine, topiramate, trimethadione, valproate, zonisamide, tetrodotoxin, and combinations thereof.

5. The lead system of claim 1, further comprising a material that is supported by the first substrate and that is different from the at least one antiepileptic agent.

6. The lead system of claim 5, wherein the at least one antiepileptic agent is dispersed or encapsulated in the material.

7. The lead system of claim 5, wherein the material is in the form of a layer over the at least one antiepileptic agent.

8. The lead system of claim 5, wherein the material comprises a polymer.

9. The lead system of claim 8, wherein the polymer is selected from the group consisting of poly (3,4-ethylenedioxythiopene), poly(3,4-ethylenedioxythiopene) poly(styrenesulfonate), and combinations thereof.

10. The lead system of claim 8, wherein the polymer is bioerodible.

11. The lead system of claim 1, wherein the at least one antiepileptic agent contacts the substrate.

12. The lead system of claim 1, wherein the at least one antiepileptic agent is in the form of a coating on the substrate.

13. A medical electrical lead system configured to be at least partially implanted in neural tissue of a subject, comprising:
   a lead body comprising a substrate;
   an electrode connected to the lead body; and
   at least one antiepileptic agent supported by the substrate of the lead body.

14. The lead system of claim 13, wherein the lead system is configured to be at least partially implanted in a brain of a subject.

15. The lead system of claim 13, wherein the lead system comprises a plurality of electrodes that are connected to the lead body.

16. The lead system of claim 13, wherein the at least one antiepileptic agent is selected from the group consisting of acetazolamide, carbamazepine, clonazepam, clorazepate, diazepam, divalproex, ethosuximide, ethotoin, felbamate, fosphenytoin, gabapentin, lamotrigine, levetiracetam, mephobarbital, methsuximide, oxcarbazepine, phenacemide, phenobarbital, phenytoin, pregabalin, primidone, thiopental, tiagabine, topiramate, trimethadione, valproate, zonisamide, tetrodotoxin, and combinations thereof.

17. A method comprising:
at least partially implanting a lead system in neural tissue of a subject,
wherein the lead system comprises a lead body, an electrode connected to the lead body and comprising a substrate, and at least one antiepileptic agent supported by a substantial portion of the area of the substrate of the electrode.

18. The method of claim 17, wherein the method comprises at least partially implanting the lead system in a brain of a subject.

19. The method of claim 17, wherein the at least one antiepileptic agent is selected from the group consisting of acetazolamide, carbamazepine, clonazepam, clorazepate, diazepam, divalproex, ethosuximide, ethotoin, felbamate, fosphenytoin, gabapentin, lamotrigine, levetiracetam, mephobarbital, methsuximide, oxcarbazepine, phenacemide, phenobarbital, phenytoin, pregabalin, primidone, thiopental, tiagabine, topiramate, trimethadione, valproate, zonisamide, tetrodotoxin, and combinations thereof.

20. The method of claim 17, wherein the lead system is configured to release the at least one antiepileptic agent when the lead system is at least partially implanted in neural tissue of a subject.

21. The method of claim 17, wherein the lead system further comprises a material that is supported by the substrate and that is different from the at least one antiepileptic agent.

22. The method of claim 21, wherein the material is bioerodible.

23. The method of claim 22, wherein erosion of the bioerodible material when the lead system is at least partially implanted in neural tissue of a subject results in the release of the at least one antiepileptic agent into the neural tissue of the subject.

24. A method comprising:
at least partially implanting a lead system in neural tissue of a subject,
wherein the lead system comprises a lead body comprising a substrate, an electrode connected to the lead body, and at least one antiepileptic agent supported by the substrate of the lead body.

25. The method of claim 24, wherein the method comprises at least partially implanting the lead system in a brain of a subject.

26. The method of claim 24, wherein the at least one antiepileptic agent is selected from the group consisting of acetazolamide, carbamazepine, clonazepam, clorazepate, diazepam, divalproex, ethosuximide, ethotoin, felbamate, fosphenytoin, gabapentin, lamotrigine, levetiracetam, mephobarbital, methsuximide, oxcarbazepine, phenacemide, phenobarbital, phenytoin, pregabalin, primidone, thiopental, tiagabine, topiramate, trimethadione, valproate, zonisamide, tetrodotoxin, and combinations thereof.

27. A method comprising:
coating a substantial portion of the area of an electrode of a medical electrical lead system with at least one antiepileptic agent, wherein the lead system comprises the electrode and a lead body connected to the electrode.

28. The method of claim 27, wherein coating the substantial portion of the area of the electrode comprises using a coating method selected from the group consisting of vapor deposition, ionic plasma deposition, dipping, and combinations thereof.

29. The method of claim 28, wherein vapor deposition comprises physical vapor deposition.

30. A method comprising:
coating a lead body of a medical electrical lead system with at least one antiepileptic agent, wherein the lead system comprises the lead body and an electrode connected to the lead body.

31. The method of claim 30, wherein coating the lead body comprises using a coating method selected from the group consisting of vapor deposition, ionic plasma deposition, dipping, and combinations thereof.

32. The method of claim 31, wherein vapor deposition comprises physical vapor deposition.

33. A medical electrical lead system configured to be at least partially implanted in neural tissue of a subject, comprising:
a lead body;
an electrode connected to the lead body and comprising a sintered metal characterized by a plurality of pores; and
an antiepileptic agent,
wherein the electrode acts as a reservoir for the antiepileptic agent and the pores in the sintered metal are adapted to release the antiepileptic agent from the reservoir into the neural tissue.

34. The lead system of claim 33, wherein the antiepileptic bioactive agent is selected from the group consisting of: acetazolamide, carbamazepine, clonazepam, clorazepate, diazepam, divalproex, ethosuximide, ethotoin, felbamate, fosphenytoin, gabapentin, lamotrigine, levetiracetam, mephobarbital, methsuximide, oxcarbazepine, phenacemide, phenobarbital, phenytoin, pregabalin, primidone, thiopental, tiagabine, topiramate, trimethadione, valproate, zonisamide, tetrodotoxin, and combinations thereof.

35. The lead system of claim 33, wherein the lead system is configured to be at least partially implanted in a brain of a subject.

36. A method comprising:
forming an electrode of a medical lead system from a sintered metal so that the electrode is characterized by a plurality of pores, wherein the lead system comprises a lead body and the electrode is configured to connect to the lead body of the lead system; and
introducing an antiepileptic agent to the electrode.

37. The method of claim 36, further comprising connecting the electrode to a lead body of the lead system.

38. The method of claim 36, further comprising releasing the antiepileptic agent from the electrode through the plurality of pores in the sintered metal.

39. The method of claim 36, wherein introducing the antiepileptic agent to the electrode comprises coating the pores of the sintered metal with the antiepileptic agent.

40. The method of claim 36, wherein the antiepileptic bioactive agent is selected from the group consisting of: acetazolamide, carbamazepine, clonazepam, clorazepate, diazepam, divalproex, ethosuximide, ethotoin, felbamate, fosphenytoin, gabapentin, lamotrigine, levetiracetam, mephobarbital, methsuximide, oxcarbazepine, phenacemide, phenobarbital, phenytoin, pregabalin, primidone, thiopental, tiagabine, topiramate, trimethadione, valproate, zonisamide, tetrodotoxin, and combinations thereof.

* * * * *